United States Patent
Udell et al.

(10) Patent No.: US 7,713,546 B1
(45) Date of Patent: *May 11, 2010

(54) COROSOLIC ACID FORMULATION AND ITS APPLICATION FOR WEIGHT-LOSS MANAGEMENT AND BLOOD SUGAR BALANCE

(75) Inventors: Ronald G. Udell, Beverly Hills, CA (US); Siva P. Hari, Riverside, CA (US)

(73) Assignee: Soft Gel Technologies, Inc., Los Angeles, CA (US)

( * ) Notice: Subject to any disclaimer, the term of this patent is extended or adjusted under 35 U.S.C. 154(b) by 94 days.

This patent is subject to a terminal disclaimer.

(21) Appl. No.: 09/825,920

(22) Filed: Apr. 3, 2001

(51) Int. Cl.
*A61K 9/64* (2006.01)
*A61K 9/00* (2006.01)
*A61K 36/00* (2006.01)

(52) U.S. Cl. .................. 424/456; 424/400; 424/725

(58) Field of Classification Search ............ 424/725
See application file for complete search history.

(56) References Cited

U.S. PATENT DOCUMENTS

| | | | |
|---|---|---|---|
| 3,665,009 A * | 5/1972 | Dickinson, Jr. .......... 548/369.7 |
| 3,683,088 A * | 8/1972 | Gregory ................. 514/410 |
| 3,886,940 A * | 6/1975 | Hunger .................. 604/288 |
| 3,950,319 A | 4/1976 | Schmidt et al. |
| 4,010,258 A | 3/1977 | Murao |
| 4,343,816 A | 8/1982 | Cavazza |
| 4,559,177 A | 12/1985 | Okutani et al. |
| 4,687,782 A | 8/1987 | Brantman |
| 4,921,475 A | 5/1990 | Sibalis |
| 5,008,110 A | 4/1991 | Benecke et al. |
| 5,030,458 A | 7/1991 | Shug et al. |
| 5,030,657 A | 7/1991 | Burtle et al. |
| 5,087,240 A | 2/1992 | Sibalis |
| 5,088,977 A | 2/1992 | Sibalis |
| 5,163,899 A | 11/1992 | Sibalis |
| 5,164,189 A | 11/1992 | Farhadieh et al. |
| 5,240,961 A | 8/1993 | Shug |
| 5,254,346 A | 10/1993 | Tucker et al. |
| 5,290,561 A | 3/1994 | Farhadieh et al. |
| 5,324,526 A | 6/1994 | Iwata et al. |
| 5,332,213 A | 7/1994 | Klose |
| 5,336,168 A | 8/1994 | Sibalis |
| 5,352,456 A | 10/1994 | Fallon et al. |
| 5,362,753 A | 11/1994 | Blum et al. |
| 5,391,550 A | 2/1995 | Carniglia et al. |
| 5,407,713 A | 4/1995 | Wilfong et al. |
| 5,431,916 A * | 7/1995 | White ..................... 424/451 |
| 5,504,072 A | 4/1996 | Schmidl et al. |
| 5,552,427 A * | 9/1996 | Matsutani et al. ......... 514/398 |
| 5,560,928 A | 10/1996 | DeFelice |
| 5,643,874 A | 7/1997 | Bremer et al. |
| 5,980,902 A * | 11/1999 | Shanmugasundaram et al. ................. 424/774 |
| 6,200,569 B1 | 3/2001 | Cheng |
| 6,200,958 B1 | 3/2001 | Odaka et al. |
| 6,203,819 B1 | 3/2001 | Fine |
| 6,248,375 B1 | 6/2001 | Gilles et al. |
| 6,303,586 B1 * | 10/2001 | McPeak et al. ............. 514/54 |
| 6,407,068 B1 * | 6/2002 | LaGrone .................. 514/21 |
| 6,485,760 B2 * | 11/2002 | Matsuyama ............... 424/775 |
| 6,572,897 B1 | 6/2003 | Gorsek |
| 6,616,942 B1 | 9/2003 | Udel et al. |
| 6,784,206 B2 * | 8/2004 | Udell et al. .............. 514/557 |
| 6,893,627 B2 | 5/2005 | Ribnicky et al. |
| 2001/0000474 A1 | 4/2001 | Matsuyama |
| 2002/0018818 A1 | 2/2002 | Suzuki et al. |
| 2003/0072822 A1 | 4/2003 | Ribnicky et al. |
| 2003/0082168 A1 | 5/2003 | Yegorva |
| 2003/0161903 A1 | 8/2003 | Konishi et al. |
| 2004/0072906 A1 | 4/2004 | Udell et al. |
| 2004/0091554 A1 | 5/2004 | Murray et al. |
| 2004/0146539 A1 | 7/2004 | Gupta |
| 2006/0051435 A1 | 3/2006 | Udell et al. |
| 2008/0152705 A1 | 6/2008 | Udell et al. |

FOREIGN PATENT DOCUMENTS

| | | |
|---|---|---|
| EP | 1166790 | 1/2002 |
| EP | 1174416 | 1/2002 |
| JP | 356032409 | 4/1981 |
| JP | 03201969 | 9/1991 |

OTHER PUBLICATIONS

Hoffman (The Complete Illustrated Herbal, Practical Herbalism, The Preparation of Herbs, 1996, pp. 20-33).*
Author Unknown, "Glucosol™ Introduction," Soft Gel Technologies, Inc. Informational Pamphlet, date unknown, at least as early as Apr. 3, 2001, Los Angeles, California, 9 pages.
Author Unknown, "Glucosol™ Clinical Study Synopsis," American Study on Balancing Blood Sugar Levels with Glucosol™, Soft Gel Technologies, Inc., date unknown, at least as early as Apr. 3, 2001, Los Angeles, California, 9 pages.
Author Unknown, "Glucosol™ Case Study Results," American Case Study on Balancing Blood Sugar Levels with Glucosol™, Soft Gel Technologies, Inc., date unknown, at least as early as Apr. 3, 2001, Los Angeles, California, 4 pages.

(Continued)

*Primary Examiner*—Christopher R Tate
*Assistant Examiner*—Randall Winston
(74) *Attorney, Agent, or Firm*—Dorsey & Whitney LLP (57) ABSTRACT

A soft gelatin capsule and method to deliver an efficable dose of *Lagerstroemia speciosa* L. (marketed by Soft Gel Technologies under the trademark Glucosol™) for the assistance and maintenance of moderate weight loss through blood sugar maintenance. The product relies on the effects of corosolic acid on blood sugar levels to derive a healthy weight loss effect for Type II diabetics (non-insulin dependent) and healthy non-diabetics and the improved absorption of an oil based delivery system. The product provides safe and sustainable weight loss when combined with a restricted calorie diet and regular exercise. Its benefits include improvement of cardiovascular health, normalized blood sugar levels, and improved physical appearance with the positive psychological effects associated with successful and safe weight loss/maintenance.

26 Claims, 6 Drawing Sheets

OTHER PUBLICATIONS

Author Unknown, "Glucosol Clinical Study Results," Presented by Chemco Industries, Inc. date unknown at least as early as Apr. 3, 2001 3 pages.

Blankson, et al, "Conjugated Linoleic Acid Reduces Body Fat Mass in Overweight and Obese Humans," American Society for Nutritional Sciences, *J. Nutr.*, 2000, vol. 130, pp. 2943-2948.

Delany, et al., "Conjugated linoleic acid rapidly reduces body fat content in mice without affecting energy intake," *Am. J. Physiol.*, 1999, vol. 276, pp. R1172-R1179.

Hayashi, et al., "Ellagitannins from *Lagerstroemia speciosa* as Activators of Glucose Transport in Fat Cells," *Planta Med.*, 2002, vol. 68, pp. 173-175.

Judy, et al., "Antidiabetic activity of a standardized extract (Glucosol™) from *Lagerstroemia speciosa* leaves in Type II diabetics. A dose-dependence study," *Journal of Ethnopharmacology*, 2003, vol. 87, pp. 115-117.

Kakuda, et al., Hypoglycemic Effect of Extracts from *Lagerstroemia speciosa* L. Leaves in Genetically Diabetic KK-AY Mice *Bioscience, Biotechnology and Biochemistry*, 1996, vol. 60, No. 2, pp. 204-208.

Liu, et al., "An Extract of *Lagerstroemia speciosa* L. Has Insulin-Like Glucose Update-Stimulatory and Adipocyte Differentiation-Inhibitory Activities in 3T3-L1 Cells," *Journal of Nutrition*, 2001, vol. 131, pp. 2242-2247.

Murakami, et al., "Screening of Plant Constituents for Effect on Glucose Transport Activity in Erhlich Ascites Tumour Cells," *Chem. Pharm. Bull.*, 1993, vol. 41, No. 12, pp. 2129-2131.

Pariza, et al., "Conjugated Linoleic Acid and the Control of Cancer and Obesity," *Toxicological Sciences*, 1999, vol. 52 (Supplement), pp. 107-110.

Park, et al., "Effect of Conjugated Linoleic Acid on Body Composition in Mice,"*Lipids*, 1997, vol. 32, No. 8, pp. 853-858.

Riserus, et al., "Conjugated linoleic acid (CLA) reduced abdominal adipose tissue in obese middle-aged men with signs of the metabolic syndrome: a randomised controlled trial," *International Journal of Obesity*, 2001, vol. 25, pp. 1129-1135.

Smedman, et al., "Conjugated Linoleic Acid Supplementation in Humans—Metabolic Effects," *Lipids*, 2001, vol. 36, No. 8, pp. 773-781.

Suzuki, et al., "Antiobesity Activity of Extracts from *Lagerstroemia Speciosa* L. Leaves on Female KK-AY Mice," *J. Nutr. Sci. Vitaminol.*, 1999, vol. 45, pp. 791-795.

Udani, et al., "Blocking Carbohydrate Absorption and Weight Loss: A Clinical Trial Using Phase 2™ Brand Proprietary Fractionated White Bean Extract," *Alternative Medicine Review*, 2004, vol. 9, No. 1, pp. 63-69.

U.S. Appl. No. 10/640,885, Preliminary Amendment dated Aug. 14, 2003, 2 pages.

U.S. Appl. No. 10/640,885, Office Action dated Apr. 20, 2004, 9 pages.

U.S. Appl. No. 10/640,885, Amendment and Response dated Jul. 15, 2004, 13 pages.

U.S. Appl. No. 10/640,885, Final Office Action dated Oct. 6, 2004, 10 pages.

U.S. Appl. No. 10/640,885, Amendment and Response dated Dec. 6, 2004, 35 pages.

U.S. Appl. No. 10/640,885, Advisory Action dated Feb. 14, 2005, 3 pages.

U.S. Appl. No. 10/640,885, Request for Continued Examination dated Feb. 28, 2005, 3 pages.

U.S. Appl. No. 10/640,885, Office Action dated May 17, 2005, 9 pages.

U.S. Appl. No. 10/640,885 Amendment and Response dated Aug. 17, 2005, 37 pages.

U.S. Appl. No. 10/640,885, Final Office Action dated Nov. 3, 2005, 9 pages.

U.S. Appl. No. 10/640,885, Amendment and Response dated Dec. 16, 2005, 40 pages.

U.S. Appl. No. 10/640,885, Advisory Action dated Feb. 8, 2006, 7 pages.

U.S. Appl. No. 10/640,885, Request for Continued Examination dated Apr. 3, 2006, 2 pages.

U.S. Appl. No. 10/640,885, Office Action dated May 16, 2006, 12 pages.

U.S. Appl. No. 10/640,885, Amendment and Response dated Sep. 15, 2006, 26 pages.

U.S. Appl. No. 10/640,885, Final Office Action dated Nov. 30, 2006, 13 pages.

U.S. Appl. No. 10/640,885, Notice of Appeal dated May 30, 2007, 2 pages.

U.S. Appl. No. 10/640,885, Request for Continued Examination and Response to Final Office Action dated Oct. 12, 2007, 14 pages.

U.S. Appl. No. 10/640,885, Final Office Action dated Jan. 2, 2008, 14 pages.

U.S. Appl. No. 10/640,885, Request for Continued Examination and Amendment dated May 2, 2008, 18 pages.

U.S. Appl. No. 10/640,885, Office Action dated Sep. 8, 2008, 22 pages.

U.S. Appl. No. 10/640,885, Response to Office Action dated Dec. 8, 2008, 19 pages.

U.S. Appl. No. 10/640,885, Final Office Action dated Mar. 18, 2009, 20 pages.

U.S. Appl. No. 10/640,885, Request for Continued Examination and Amendment dated Jul. 14, 2009, 19 pages.

U.S. Appl. No. 10/640,886, Preliminary Amendment dated Aug. 14, 2003, 4 pages.

U.S. Appl. No. 10/640,886, Notice of Allowance and Fee(s) Due dated May 19, 2004, 7 pages.

U.S. Appl. No. 10/640,886, Issue Fee Transmittal dated May 27, 2004, 3 pages.

U.S. Appl. No. 11/470,527, Preliminary Amendment dated Sep. 6, 2006, 6 pages.

U.S. Appl. No. 11/470,527, Office Action dated Aug. 6, 2009, 6 pages.

U.S. Appl. No. 11/205,789, Preliminary Amendment dated Sep. 21, 2005, 8 pages.

U.S. Appl. No. 11/205,789, Office Action (Restriction Requirement) dated Sep. 24, 2007, 6 pages.

U.S. Appl. No. 11/205,789, Response to Restriction Requirement dated Oct. 24, 2007, 10 pages.

U.S. Appl. No. 11/205,789, Office Action dated Dec. 14, 2007, 12 pages.

U.S. Appl. No. 11/205,789, Amendment and Response to Office Action dated Mar. 14, 2008, 10 pages.

U.S. Appl. No. 11/205,789, Final Office Action dated Jun. 3, 2008, 10 pages.

U.S. Appl. No. 11/205,789, Amendment After Final dated Oct. 13, 2008, 10 pages.

U.S. Appl. No. 11/205,789, Advisory Action dated Oct. 31, 2008, 3 pages.

U.S. Appl. No. 11/205,789, Request for Continued Examination and Amendment After Final dated Dec. 3, 2008, 14 pages.

U.S. Appl. No. 11/205,789, Final Office Action dated Jan. 27, 2009, 12 pages.

U.S. Appl. No. 11/205,789, Request for Continued Examination and Amendment After Final dated Jul. 27, 2009, 19 pages.

\* cited by examiner

SIBR INC - SOFT GEL TECHNOLOGIES GLUCOSOL STUDY
GLUCOSOL - BLOOD GLUCOSE STUDY SIBR 08-99

| DAYS | CONTROL | 48 mg/DAY SOFTGEL | | GLUCOSOL WASHOUT | | | 48 mg/DAY POWDER | | | GLUCOSOL WASHOUT | | |
|---|---|---|---|---|---|---|---|---|---|---|---|---|
| VOLUNTEERS | -7 | 0 | 15 | 30 | 45 | 60 | 75 | 90 | 105 | 120 | 135 | 150 |
| 1 | 174 | 168 | 115 | 106 | 120 | 146 | 176 | 124 | 123 | 139 | 148 | 162 |
| 2 | 190 | 182 | 140 | 136 | 138 | 160 | 184 | 136 | 134 | 130 | 155 | 185 |
| 3 | 173 | 163 | 118 | 92 | 118 | 141 | 160 | 136 | 130 | 144 | 154 | 167 |
| 4 | 149 | 150 | 117 | 110 | 122 | 155 | 166 | 135 | 129 | 139 | 147 | 152 |
| 5 | 164 | 163 | 125 | 116 | 115 | 136 | 155 | 114 | 110 | 114 | 133 | 160 |
| 6 | 178 | 183 | 127 | 115 | 138 | 158 | 180 | 146 | 140 | 158 | 166 | 178 |
| 7 | 170 | 175 | 129 | 119 | 148 | 168 | 180 | 148 | 133 | 149 | 156 | 177 |
| 8 | 154 | 161 | 117 | 96 | 110 | 160 | 160 | 136 | 128 | 140 | 158 | 170 |
| 9 | 186 | 179 | 155 | 144 | 142 | 156 | 168 | 144 | 138 | 145 | 150 | 172 |
| 10 | 160 | 157 | 121 | 111 | 135 | 146 | 155 | 135 | 128 | 148 | 163 | 170 |
| 11 | 159 | 166 | 133 | 116 | 138 | 152 | 166 | 143 | 137 | 145 | 158 | 166 |
| 12 | 168 | 172 | 129 | 120 | 148 | 160 | 168 | 136 | 132 | 146 | 156 | 168 |
| MEAN | 168.8 | 168.3 | 127.2 | 115.1 | 131.7 | 153.2 | 168.2 | 136 | 130.2 | 141.4 | 153.7 | 168.9 |
| SD | 12.4 | 10.3 | 11.56 | 14.6 | 13.2 | 9.3 | 9.9 | 9.4 | 7.9 | 10.9 | 8.6 | 8.8 |
| SE | 3.6 | 3 | 3.3 | 4.2 | 3.8 | 2.7 | 2.9 | 2.7 | 2.3 | 3.2 | 2.5 | 2.5 |
| VAR | 153 | 104.9 | 132.4 | 212.4 | 175.5 | 85.6 | 98.3 | 89.6 | 63.6 | 120.5 | 73.3 | 76.8 |

INFLUENCE OF SOFTGEL AND POWDER GLUCOSOL (48mg/DAY) ON BLOOD SUGAR LEVELS IN TYPE II DIABETICS. NOTE THE RAPID BLOOD SUGAR REDUCTION DURING SUPPLEMENTATION AND THE SLOW RECOVERY DURING GLUCOSOL WASHOUT

Fig. 3

BLOOD SUGAR LOWERING EFFECTS OF SOFTGEL AND POWDER GLUCOSOL. BOTH GLUCOSOL FORMS SIGNIFICANTLY ($p < 0.01$) LOWERED BLOOD SUGARS IN 15 AND 30 DAYS. THE RECOVERY TIME WAS DELAYED WITH BOTH GLUCOSOL FORMS.

Fig. 4

BODY WEIGHT CHANGES BEFORE AND AFTER 48 mg/DAY OF SOFTGEL OR POWDER GLUCOSOL. NOTE THE ACUTE DROP IN WEIGHT DURING GLUCOSOL SUPPLEMENTATION AND THE SLOW WEIGHT GAIN DURING THE WASHOUT INTERVALS. THE WEIGHT LOSS WITH 48 mg/DAY SOFTGEL OR POWDER GLUCOSOL WAS NOT REGAINED IN SIX WEEKS. THUS, THE BASELINE WEIGHT FOR THE POWDER GLUCOSOL (DAY 75) WAS LOWER THAN THAT FOR THE SOFTGEL FORMULATION (DAY 0).

SIBR INC - SOFT GEL TECHNOLOGIES GLUCOSOL STUDY
GLUCOSOL - BODY WEIGHT STUDY: SIBR 05-99

| EVENT | CONTROLS | 48 mg/DAY SOFTGEL | | | WASHOUT | | 48 mg/DAY POWDER | | | WASHOUT | |
|---|---|---|---|---|---|---|---|---|---|---|---|
| DAYS | -7 | 0 | 15 | 30 | 45 | 60 | 75 | 90 | 105 | 120 | 135 |
| VOLUNTEER | | | | | | | | | | | |
| 1 | | 2 | 0 | -2 | -1 | -1 | -2 | -1 | -2 | -3 | -2 |
| 2 | | 0 | -2 | -4 | -5 | -4 | -4 | -5 | -6 | -5 | -5 |
| 3 | | -1 | -1 | -2 | -3 | -2 | -2 | -2 | -3 | -3 | -4 |
| 4 | | -1 | 0 | -1 | -2 | -2 | -3 | -3 | -5 | -4 | -5 |
| 5 | | -1 | -1 | -2 | -3 | -3 | -1 | -5 | -1 | -2 | -1 |
| 6 | | -1 | -2 | -4 | -4 | -4 | -5 | -2 | -4 | -4 | -3 |
| 7 | | -1 | 0 | -3 | -1 | 0 | 0 | -4 | -3 | -2 | -3 |
| 8 | | -1 | -1 | -1 | -2 | -3 | -2 | -4 | -5 | -7 | -1 |
| 9 | | -1 | -2 | -1 | -2 | -2 | -2 | -4 | -5 | -6 | -8 |
| 10 | | -1 | -2 | -4 | -3 | -4 | -5 | -4 | -5 | -5 | -5 |
| 11 | | -1 | -1 | -1 | -2 | -2 | -2 | -4 | -5 | -5 | -5 |
| 12 | | 0 | -3 | -4 | -5 | -4 | -5 | -6 | -8 | -7 | -7 |
| MEANS | | 0.25 | -1.25 | -2.25 | -3 | -2.91 | -2.58 | -3.17 | -4 | -4.33 | -4.1 |
| SD | | 1.06 | 0.96 | 0.96 | 1.48 | 1.56 | 1.92 | 1.94 | 2.24 | 1.72 | 2.2 |
| SE | | 0.3 | 0.28 | 0.27 | 0.42 | 0.45 | 0.55 | 0.56 | 0.65 | 0.5 | 0.63 |

0 DAY COMPARISON: $p < 0.05$   $p < 0.05$   $p < 0.001$   $p < 0.001$   $p < 0.001$   $p < 0.001$   $p < 0.001$   $p < 0.001$   $p < 0.001$

75 DAY COMPARISON: $p < 0.24$   $p < 0.07$   $p < 0.003$   $p < 0.02$

Fig. 5

Fig. 6

COROSOLIC ACID FORMULATION AND ITS APPLICATION FOR WEIGHT-LOSS MANAGEMENT AND BLOOD SUGAR BALANCE

FIELD OF THE INVENTION

This invention relates to an improved food supplement formulation including Corosolic acid for producing sustained weight-loss management and blood sugar balance effects. This food supplement further aims to improve high blood sugar levels in subjects suffering from Type 2 diabetes or non-insulin dependent diabetes mellitus (NIDDM).

BACKGROUND OF THE INVENTION

The first diagnosis of diabetes dates back to Greece, 2,000 years ago. Blood sugar balance, in general, diabetes, in particular, ever since has been the subject of an increasing scientific study. Diabetes affects 16 million people in the United States alone and it is the fourth leading cause of death. Insulin, the hormone produced by pancreas, regulates the uptake and conversion of sugar into heat energy and muscle power. Diabetes is a metabolic disorder and insufficient insulin production leads to Type 1 diabetes or insulin-dependent diabetes mellitus (IDDM). Lipid metabolism is often deranged in diabetics resulting in weight gain and other complications.

More than half of U.S. adults are overweight (body mass index, BMI<25), one-quarter is obese (BMI<30), and 11% of children and adolescents are overweight. Approximately 280,000 deaths are attributable to obesity annually. Sedentary life style is prevalent and only 22% of U.S. adults exercise the recommended five times per week for at least 30 minutes. Healthy weight maintenance involves a delicate balance between energy intake and energy expenditure.

Glucose is the principal nutrient for energy and daily energy balance between intake and expenditure is a determining factor in body weight stability. A long-term positive energy balance leads to weight gain, while a negative balance accounts for weight loss. Obesity is an alarming trend globally and more acute in developed countries due to sedentary life style and rich diets among both adults and children and leads to deleterious consequences such as obesity, syndrome X, insulin resistance, diabetes and other health risks (York D, Bouchard C. How obesity develops, Endocrine, 13 (2), 143-154, 2000). Syndrome X is a metabolic disorder characterized by insulin resistance and central obesity, high cholesterol, high blood pressure and high blood sugar levels. An estimated 20 to 30% of middle-aged Americans suffer from Syndrome X, which is believed to increase risk for diabetes and heart disease. The spread of obesity is considered to be an epidemic in the U.S. and a sensible, sustained weight management is a critical step in this environment (Mokdad A H, Serdula M K, Dietz W H, Bowman B A, Marks J S, Koplan J P. The spread of the obesity epidemic in the United States, 1991-1998, JAMA, 282 (16), 1519-1522, 1999).

Glucose is the most important nutrient for many cells of the body. Glucose transport from the blood into cells, therefore, is one of the most important functions of all cells and some tissues, such as brain, are solely dependent on glucose as an energy source. Insulin regulates glucose uptake into fat and muscle cells through the recruitment of glucose transporter (GLUT)4 from an intracellular membrane storage pool to the plasma membrane. A complex homeostatic mechanism keeps the blood glucose level constant in mammals and most cells contain several types of sodium linked glucose transporters known as GLUT family. Glucose transporters, such as GLUT4, are especially important for regulating intracellular glucose in heart and skeletal muscle cells and in fat cells (brown and white adipocytes). The pancreatic hormone insulin regulates blood sugar levels by a cascade of biochemical steps, including activation and translocation of GLUT4 to cell surface, for glucose transport from blood to cells (Yamasaki K, Effects of some saponins on glucose transport system, Eds. Waller and Yamasaki, 1996. Plenum Press, New York; Maier V H and Gould G W. Long-term insulin treatment of 3T3-L1 adipocytes results in mistargeting of GLUT4: implications for insulin-stimulated glucose transport, Diabetologia, 43, 1273-1281, 2000; Yaworsky K, Somwar R, Ramlal T, Tritschler H J, Klip A. Engagement of insulin-sensitive pathway in the stimulation of glucose transport by a-lipoic acid in 3T3-L1 adipocytes, Diabetologia, 43, 294-303, 2000).

Numerous groups have been systematically searching for an agent to modify glucose transport activity and to find a natural product useful as an anti-diabetic agent. Various medicinal plants from Asia have been used to treat diabetes and the plants exhibiting hypoglycemic effect include *Momordica Charantia, Tinospora Cordifolia, Ginseng*, etc. (Yamasaki K 1996). Tea preparations from the leaves of *Lagerstroemia Speciosa* L., traditionally have been urea for weight-loss and by diabetics to balance blood sugar levels (Murakami C, Myoga K, Ryoji K, Ohtani K, Kurokawa T, Ishibashi S, Dayrit F, Padolina W G and Yamasaki, K. Screening of plant constituents for effect on glucose transport activity in Ehrlich Ascites tumor cells, Chemical and Pharmaceutical Bulletin, 41 (12), 2129-2131, 1993) and in-vitro studies indicate that Corosolic acid extracted from the leaves of *Lagerstroemia Speciosa* L, improves the cellular uptake of glucose (Murakami C. et al. 1993). Further studies in diabetic mice indicate the hypoglycemic effects of leaf-extracts from Lagerstroemia Speciosa L. (Kakuda T, Sakane I, Takihara T, Ozaki Y, Takeuchi H and Kuroyanagi M. Hypoglycemic effect of extracts from *Lagerstroemia speciosa* L. leaves in genetically diabetic KK-AY mice, Biosci. Biotech. Biochem., 60 (2), 204-208, 1996).

SUMMARY OF THE INVENTION

The present invention comprises a stable and non-toxic Corosolic acid formulation including a soft gel formulation for increased absorption of Corosolic acid into the human body. A preferred soft gel formulation includes Corosolic acid, rice bran oil, and yellow bee's wax or silica. The preferred soft gel Corosolic acid formulation is administered thrice a day in dosages of about 16 mg.

DETAILED DESCRIPTION OF THE PREFERRED EMBODIMENTS

Corosolic acid (2-a-hydroxyursolic acid, CAS# 52213-27-1; Glucosol™ (trademark of Soft Gel Technologies, Inc. of Los Angeles, Calif.) is a triterpenoid with a molecular weight of 743.63 grams and is a lipophilic, polar compound that is extracted from the leaves of *Lagerstroemia Speciosa* L. *Lagerstroemia Speciosa* L. is commonly known as Crepe Myrtle and belongs to the botanical family lythraceae. It is a very common ornamental deciduous tree that grows in the tropical areas of the globe. Tea preparations from the leaves of *Lagerstroemia Speciosa* L., traditionally have been used for weight-loss and by diabetics to balance blood sugar levels (Murakami et. al., 1993).

Both in-vitro and in-vivo studies on the glucose transporter stimulatory effects of extracts from *Lagerstroemia Speciosa* L., have been described previously, including the identification of Corosolic acid (2-a-hydroxyursolic acid, CAS# 52213-27-1), a triterpenoid, as the active principle of this extract and its hypoglycemic effect (Murakami et. al., 1993; Yamasaki, 1996; De Tommasi N, De Simone W I, Ho F, Sirino G, Cicala C, Pizza C, Hypoglycemic effects of sesquiterpene glycosides and polyhydroxylated triterpenoids of Eriobotrya japonica, Planta Meica, 57, 414, 1991; Garcia, F. On the Hypoglycemic Effect of Decoction of *Lagerstroemia Speciosa* leaves (Banaba) Administered Orally. *The Journal of the Philippine Medical Association*, 22, #7, 395402, 1940; Garcia, F. Distribution and Deterioration of Insulin-like Principle in *Lagerstroemia Speciosa* (Banaba). *Acta Medica Philippina*, 99-104; Garcia, F., and Melencio-Maglalang, P. Application of Banabins (A Plantisul Preparation) and S.B. Menus to Diabetics. *The Journal of the Philippine Medical Association*, 33, #1, 7-16, 1957; Garcia, F. Criticisms and Answers on Published Articles concerning Banabins or Plantisul Tablets. *The Journal of the Philippine Medical Association*, 35, #5, 313-319, 1959; Garcia, L., Pojas, F., Castro, I., Verizon, E., Sisson, F. and Capal, T. Pharmaccutico-chemical and Pharmacological Studies on a Crude Drug from *Lagerstroemia Speciosa*. *The Philippine Journal of Science*, 116, #4, 361-375, 1987; Scalori V et al., Int. J. Tiss. Reac., 1983, X 2, 95-97). Furthermore, according to the descriptions in the following references, extracts from these plants administered to rats at 10 mg/kg caused significant reduction in blood sugar levels. Acute toxicity studies in rats based on a single oral limit-dose of 5 g/Kg conclude that Corosolic acid is safe and non-toxic.

The following clinical study was conducted using the soft-gelatin capsule formulation of Corosolic acid (Glucosol™) to evaluate the hypoglycemic and weight loss effects in Type 2 diabetics. Additional studies were conducted in normal subjects to compile the safety and weight loss effects of Corosolic acid.

Blood glucose balance and weight-loss:

A group of 12 subjects with a history of type 2 diabetes (six men of age range 57 to 76 and body weight range of 171 to 238 pounds and six women ranging in 55 to 70 years of age with a weight range of 154 to 189 pounds) were given an oral daily dose of 48 mg Glucosol™ in a soft gel formulation for 30 days followed by a 45 day wash-out period. The same group was crossed over to an oral daily dose of 48 mg Glucosol™ in a hard gel capsule formulation for 30 days followed by a 45 day wash-out period. Each volunteer provided a blood sample in the morning, after an over night fast, seven days before the start of the study (−7 day) and on the day of the study (0 day) to evaluate the basal blood glucose levels. Subsequently, blood glucose level and body weight were measured at 15-day interval for the duration of the study.

Figure 1:
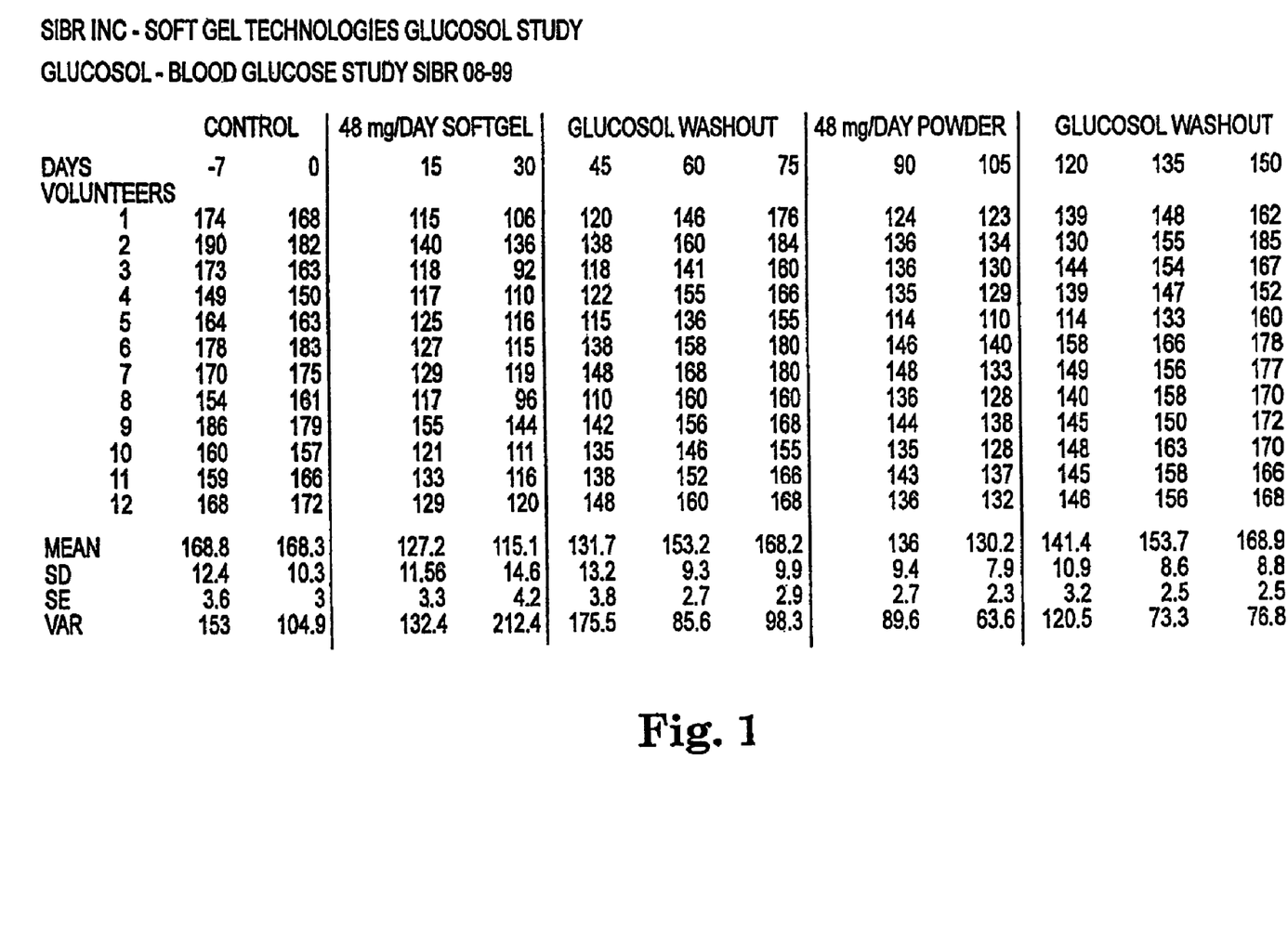
FIG. 1 is a numerical comparison of the sugar levels in volunteers raking nothing, Corosolic acid in gel form and Corosolic acid in powder form.
Figure 2:
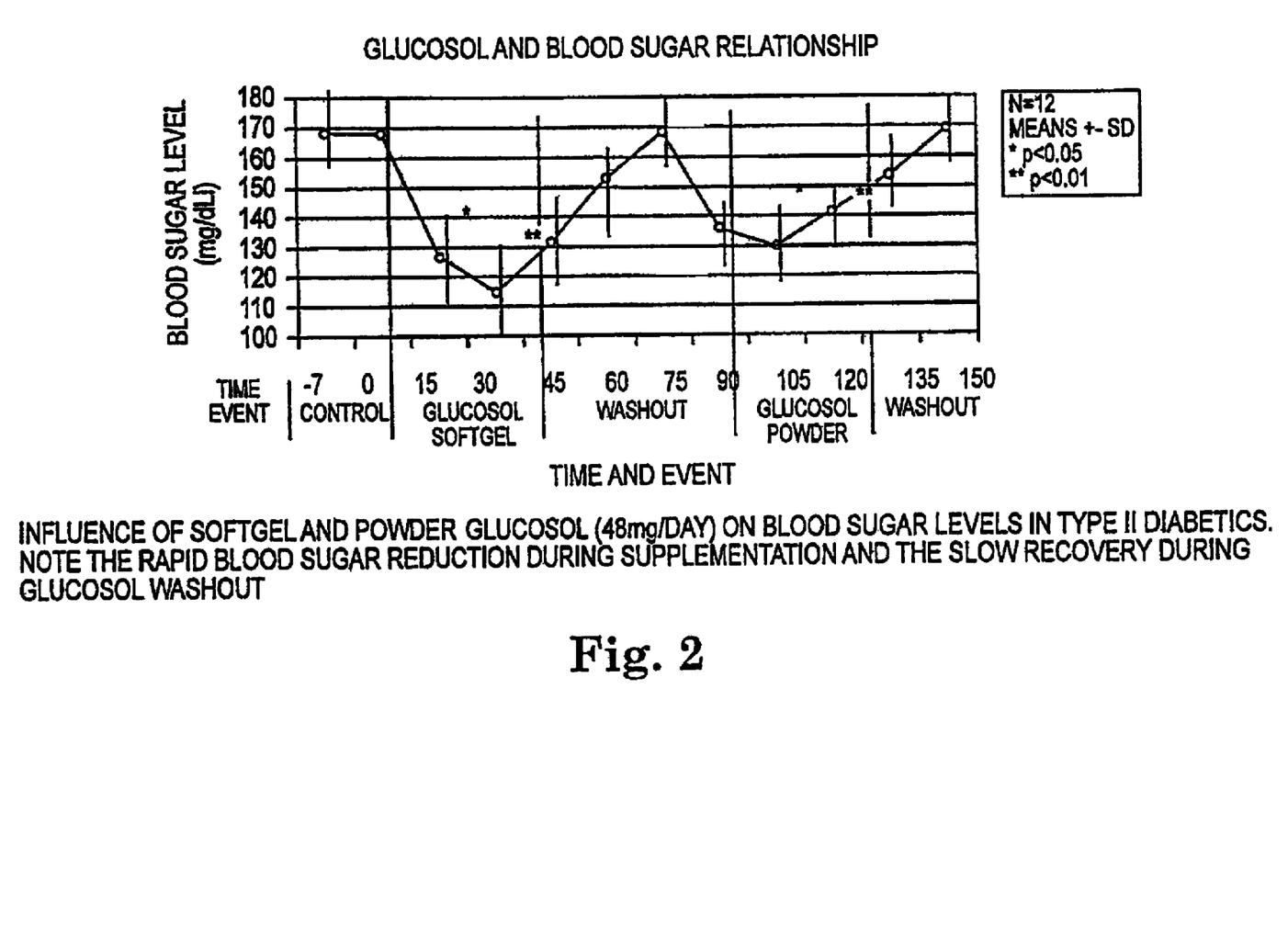
FIG. 2 is a graph showing the washout rates of blood sugar level vs. time during and after taking gel and powder Corosolic acid.
Figure 3:
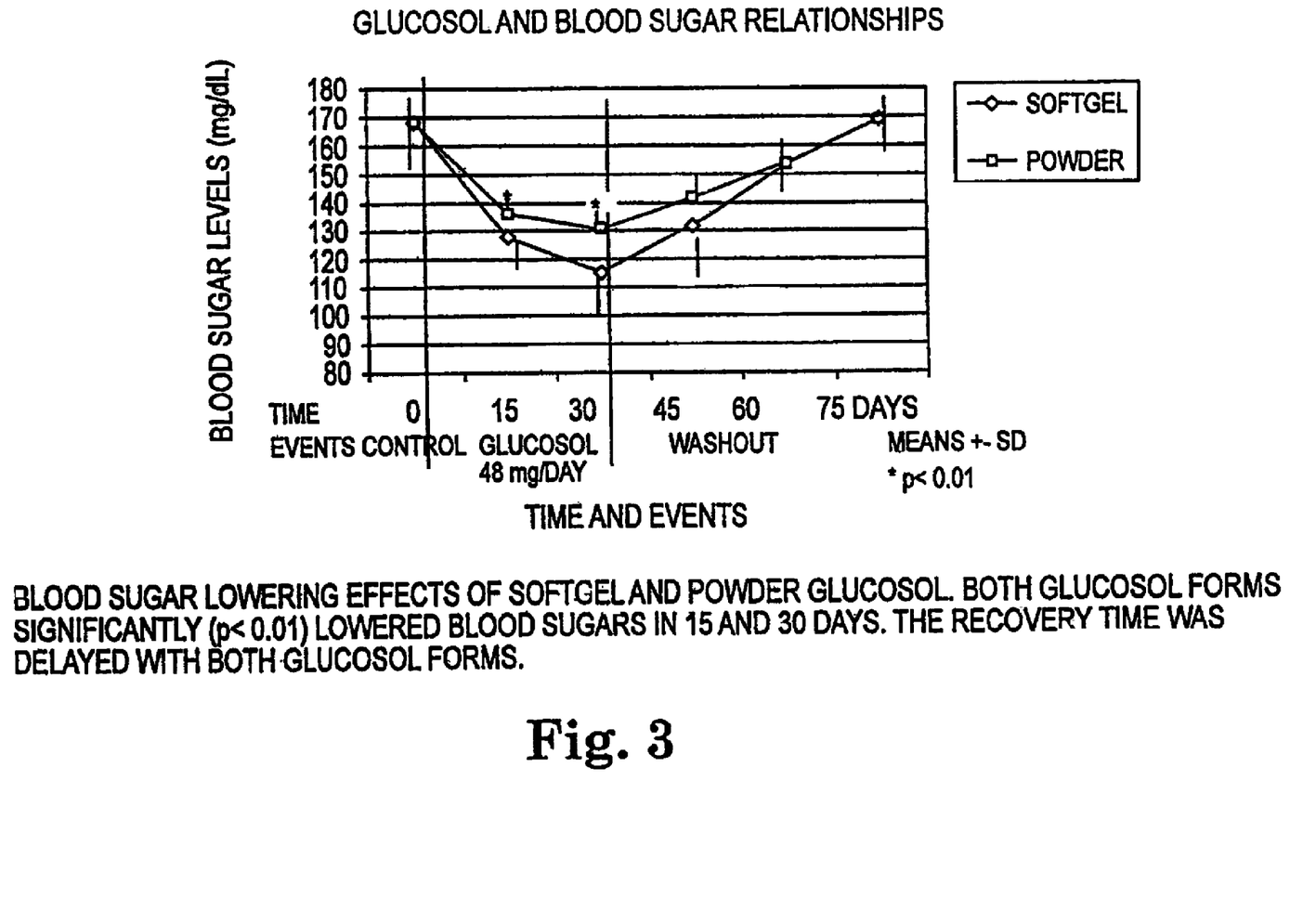
FIG. 3 is a comparison graph showing the blood sugar level vs. time during and after taking gel and powder Corosolic acid.
Figure 4:
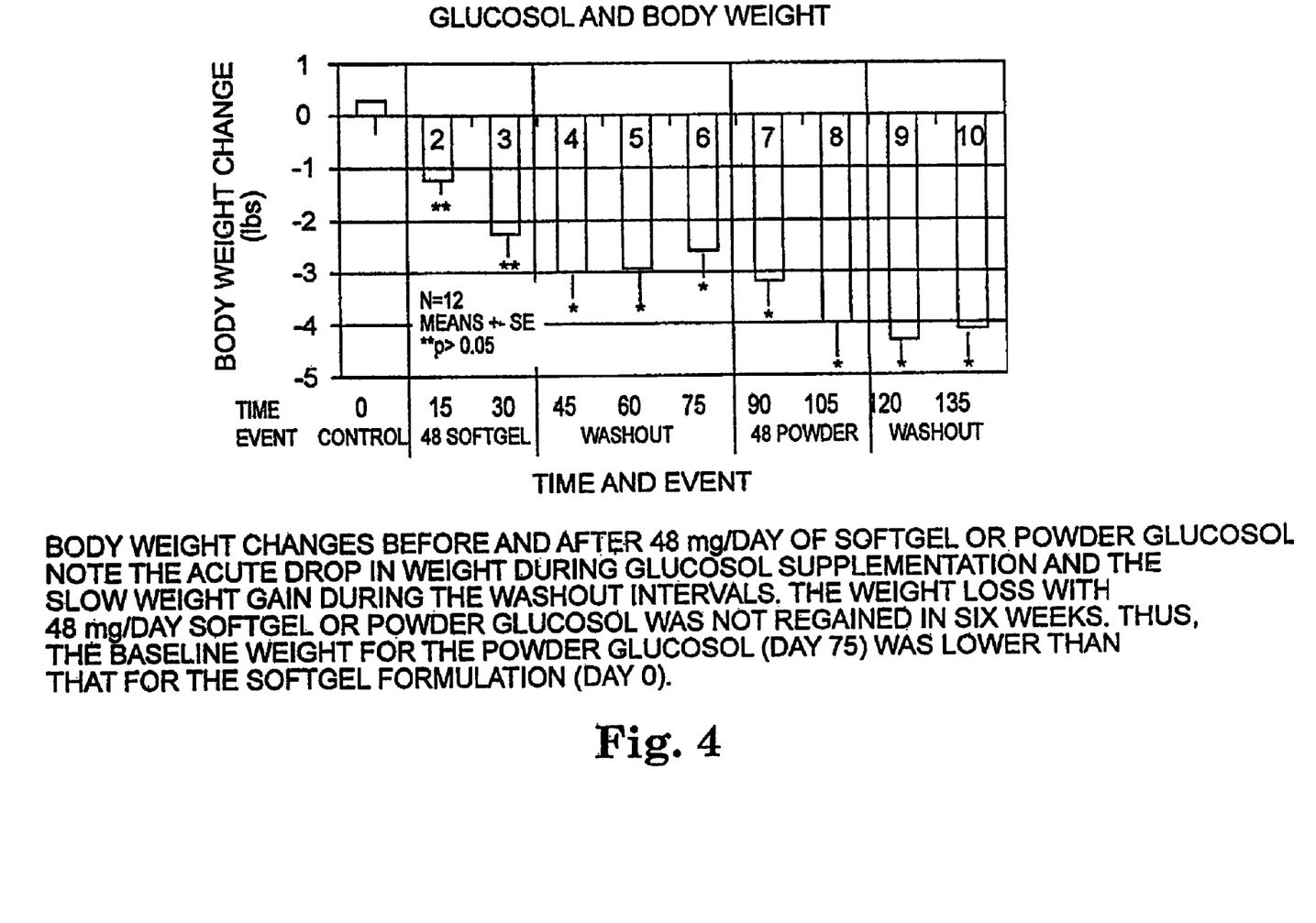
FIG. 4 is a graph showing the washout rates of weight vs. time during and after taking gel and powder Corosolic acid.

Blood glucose balance and weight-loss:

In this 30-day study, at a daily dose of 48 mg of Glucosol™, both soft gel and dry-powder hard gel formulations show a statistically significant ($p<0.001$) decrease in blood glucose levels compared to control blood glucose measurements (FIGS. 1, 2, and 3). Compared on control levels, the relative reduction in blood glucose level was similar to that observed in the dose-response study; 31.5% decrease in the soft gel and 22.6% decrease in the hard gel formulation. However, compared to the dry-powder hard gel formulation, the soft gel form of Glucosol™ shows a significantly ($p<0.01$) greater ability to lower blood glucose levels. Further, the slow recovery of blood glucose levels during the wash-out period for both formulations suggests an after-effect or memory-effect of Glucosol™, even after the cessation of the daily dose of Glucosol™ which suggests a significant implication for daily-dose compliance issue for diabetics.

Figure 5:
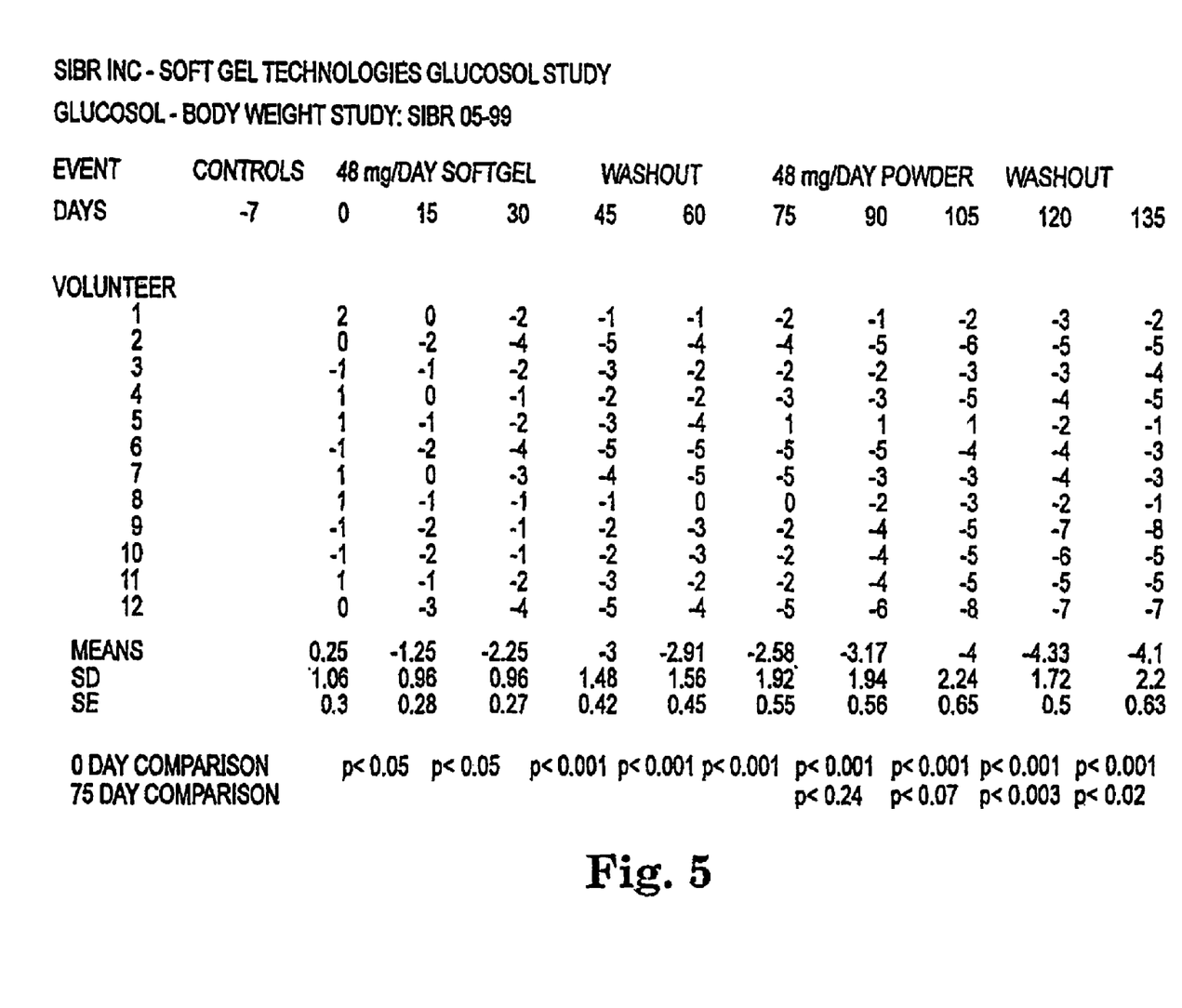
FIG. 5 is a numerical comparison of the weight of volunteers taking nothing, Corosolic acid in gel form and Corosolic acid in powder form.
Figure 6:
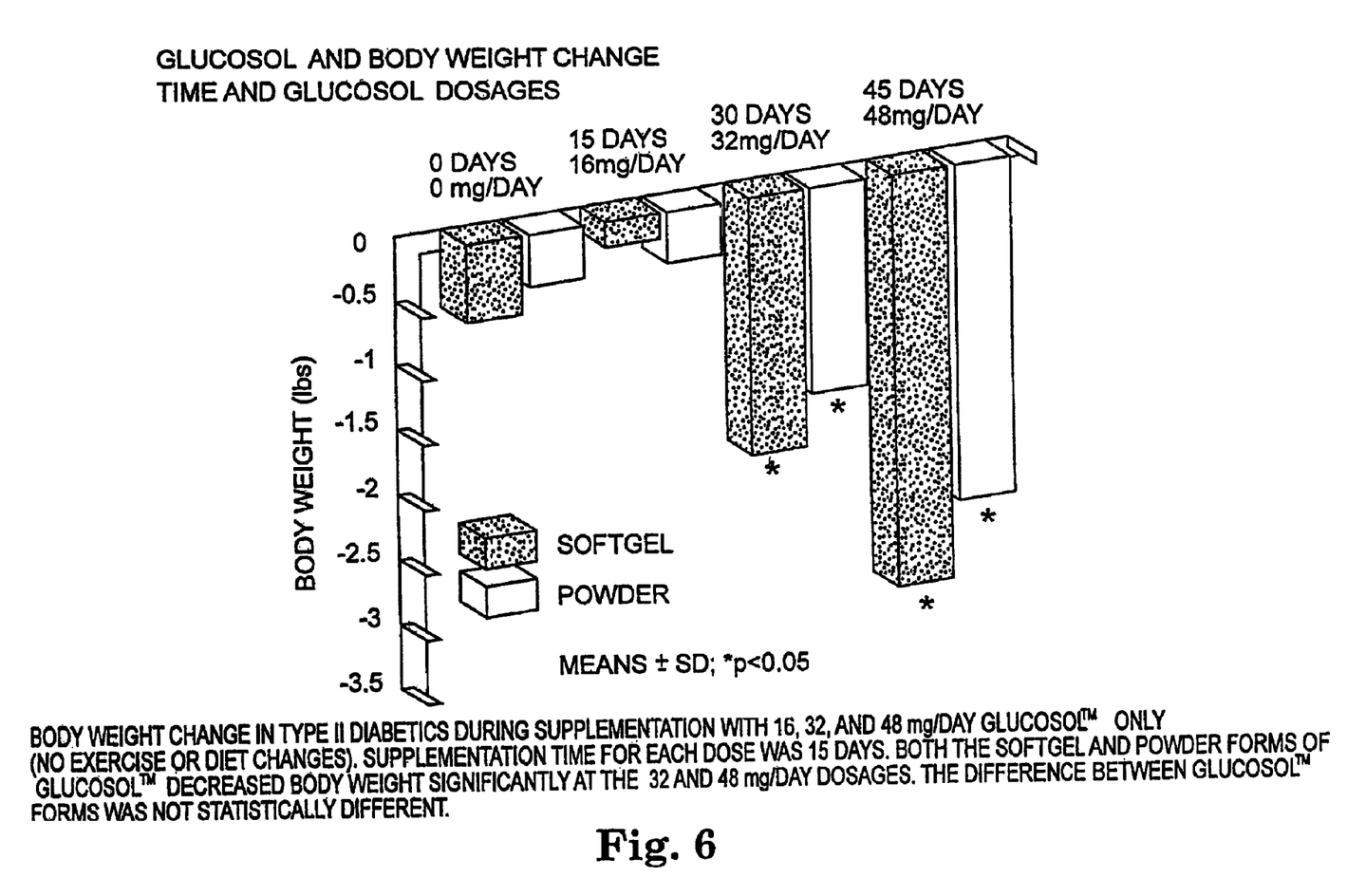
FIG. 6 is a graph of weight change vs. dosage of Corosolic acid.

Concurrent with the reduction of blood glucose levels, a weight-loss was observed in both formulations of Glucosol™ (FIGS. 5 and 6). Further, the weight-gain during the wash-out period was significantly slower confirming the after-effect or memory-effect of Glucosol™. Weight-loss was also observed during the dose-response study. The differences in weightloss between the soft gel and hard gel formulations are significant at 32 and 48 mg/day Glucosol™ doses (FIG. 6).

Acute and chronic clinical studies of Corosolic acid (Glucosol™) formulations in normal subjects at daily dose of 48 mg Glucosol™ indicate that their blood sugar levels remain in the normal range (75 to 110 mg/dL) before, during and after the intake of Glucosol™. Furthermore, blood chemistry and hematology profiles did not suggest any significant changes indicating the safety profile of Glucosol™. The only significant finding is a weight loss observed in normal subjects receiving Glucosol™ at 48 mg per day for 30 days. The mean body weight-loss was 1.25+0.6 pounds after 15 days and 2.4+0.8 pounds after 30 day use of Glucosol™.

Therefore, oral formulations of leaf extract of *Lagerstroemia speciosa* L. standardized to 1% Corosolic acid (Glucosol™) exert a marked lowering of blood sugar in type 2 diabetics and also a significant and sustained weight-loss without any adverse effects. Further, the results of this study indicate that Glucosol™ does not alter either the absorption or clearance of blood sugar in non-diabetic subjects, while retaining its weight-loss effect.

Glucosol™ formulated in a soft gelatin capsule demonstrated a significant improvement in blood sugar lowering or weight-loss effect compared to Glucosol™ formulated in a dry-powder hard gelatin capsule suggesting that the triterpene active ingredient in Glucosol™ is lipophilic and better absorbed in an oil-based soft gelatin capsule formulation.

Although Glucosol™ shows a significant dose-response relationship over the range of 16 to 48 mg per day, the top of the dose-response curve may not have been achieved so the maximum dose to achieve a leveling-off response is unknown.

It is an objective of the present invention to provide an improved formulation of Corosolic acid, including a soft gel formulation that produce a significant and sustained weight-loss and an optimal blood sugar balance. To this end, this formulation contains *Lagerstroemia speciosa* L. standardized to 1% Corosolic acid (Glucosol™) and refined soybean oil.

It is a further objective of the present invention to provide a soft gel formulation of Corosolic acid and administration that produces greater absorption into the intestine.

The unique formulation involves the following sequence of ingredients.

1. Rice bran oil to be heated to 35° C.

2. Addition of Yellow Bees wax or silica.

3. Simultaneous addition under vacuum of the following ingredient: Glucosol™ (normally an alcohol extract 1% Corosolic acid but an aqueous alcohol seems to have the same effects).

4. Blending and continuous stirring of all the ingredients.

5. Cooling of the mixture to room temperature (about 22° C.).

6. Thorough mixing and nitrogen gas blanketing of the container.

7. Soft gel capsulation of the above mixture.

In summary, previous in-vitro, pre-clinical (animal) and clinical studies with various preparations of *Lagerstroemia speciosa* L, indicate the beneficial effects of blood-sugar lowering and anecdotal weight-loss effects. Present clinical studies establish the dose-response relationship of *Lagerstroemia speciosa* L. standardized to 1% Corosolic acid (Glucosol™) formulated into a soft gelatin capsule dosage form. Additional studies with this new formulation in a clinical setting suggest improved bioavailability and absorption of Corosolic acid in an oil-based soft gel capsule formulation compared to a dry-powder hard gelatin capsule formulation.

In addition, the present invention may also incorporate an extract of *Gymnema sylvestre*, an herb also helpful for weight loss through blood glucose control, as additional ingredient. The present invention may also include a multi herb formulation, with the addition of antioxidant vitamins C and E, B complex vitamins, as well as the nutrients Alpha Lipoic Acid, $CoQ_{10}$, and the mineral chromium, since all are useful in a balanced weight loss program.

Thus there has been shown and described novel formulations, methods, and capsules, which fulfill all the objects and advantages sought therefor. Many changes, modifications, variations and applications of the subject invention will become apparent to those skilled in the art after consideration of the specification and the accompanying Figures. All such changes, modifications, alterations and other uses and applications which do not depart from the spirit and scope of the invention are deemed to be covered by the invention which is limited only by the claims that follow:

The invention claimed is:

1. A unitary soft gel capsule for oral administration, prepared by a process comprising the steps of:
   heating an oil in a container;
   adding filler to provide a mixture;
   adding Corosolic acid;
   stirring the mixture; and
   encapsulating the mixture in a soft gel capsule.

2. The soft gel capsule of claim 1, wherein the filler comprises yellow bee's wax.

3. The soft gel capsule of claim 1, wherein the filler comprises silica.

4. The soft gel capsule of claim 1, wherein the filler comprises yellow bee's wax and silica.

5. The soft gel capsule of claim 1, wherein the Corosolic acid is 1% Corosolic acid.

6. The soft gel capsule of claim 1, wherein the oil is rice bran oil.

7. The soft gel capsule of claim 1, wherein the Corosolic acid is present in the range of 8 to 100 mg.

8. The soft gel capsule of claim 1, further comprising adding an extract of *Gymnema sylvestre* to the mixture.

9. The soft gel capsule of claim 1, wherein the Corosolic acid is added under a vacuum.

10. The soft gel capsule of claim 1, wherein the mixture is blanketed with nitrogen.

11. The soft gel capsule of claim 1, wherein the filler comprises yellow bee's wax and silica and the Corosolic acid is 1% Corosolic acid.

12. The soft gel capsule of claim 11, wherein the Corosolic acid is added under a vacuum.

13. The soft gel capsule of claim 12, wherein the mixture is mixed under nitrogen.

14. A method for preparing a Corosolic acid soft gel capsule comprising:
   heating an oil in a container;
   adding filler to provide a mixture;
   adding Corosolic acid;
   stirring the mixture; and
   encapsulating the mixture in a soft gel capsule.

15. The method of claim 14, wherein the filler comprises yellow bee's wax.

16. The method of claim 14, wherein the filler comprises silica.

17. The method of claim 14, wherein the filler comprises yellow bee's wax and silica.

18. The method of claim 14, wherein the Corosolic acid is 1% Corosolic acid.

19. The method of claim 14, wherein the oil is rice bran oil.

20. The method of claim 14, wherein the Corosolic acid is present in the range of 8 to 100 mg.

21. The method of claim 14, further comprising adding an extract of *Gymnema sylvestre* to the mixture.

22. The method of claim 14, wherein the Corosolic acid is added under a vacuum.

23. The method of claim 14, wherein the mixture is blanketed with nitrogen.

24. The method of claim 14, wherein the filler comprises yellow bee's wax and silica and the Corosolic acid is 1% Corosolic acid.

25. The method of claim 24, wherein the Corosolic acid is added under a vacuum.

26. The method of claim 25, wherein the mixture is mixed under nitrogen.

* * * * *